(12) United States Patent
Astley et al.

(10) Patent No.: US 6,999,884 B2
(45) Date of Patent: Feb. 14, 2006

(54) BEARING ANOMALY DETECTION AND LOCATION

(75) Inventors: Kenneth Richard Astley, Derby (GB); Paul Anuzis, Derby (GB); Stephen Peter King, Derby (GB); Dennis Maxwell King, Derby (GB)

(73) Assignee: Oxford Biosignals Limited, Oxford (GB)

( * ) Notice: Subject to any disclaimer, the term of this patent is extended or adjusted under 35 U.S.C. 154(b) by 0 days.

(21) Appl. No.: 10/734,152

(22) Filed: Dec. 15, 2003

(65) Prior Publication Data

US 2005/0119840 A1    Jun. 2, 2005

Related U.S. Application Data

(60) Provisional application No. 60/439,026, filed on Jan. 10, 2003.

(51) Int. Cl.
*G06F 19/00* (2006.01)
*G05B 13/00* (2006.01)
*G01N 29/04* (2006.01)

(52) U.S. Cl. .............................. 702/56; 73/660; 706/20
(58) Field of Classification Search ................ 702/34, 702/42, 56, 57, 190; 73/660; 706/20; 700/71; 340/683
See application file for complete search history.

(56) References Cited

U.S. PATENT DOCUMENTS

| 5,206,816 A | 4/1993 | Hill et al. ....................... 702/56 |
| 5,210,704 A | 5/1993 | Husseiny ....................... 702/34 |
| 5,402,521 A | 3/1995 | Niida et al. .................... 706/20 |
| 5,684,718 A | 11/1997 | Jenkins et al. ................. 702/57 |
| 5,774,376 A | 6/1998 | Manning ....................... 702/56 |
| 5,784,273 A | 7/1998 | Madhavan .................... 700/71 |
| 5,811,683 A * | 9/1998 | Yoshioka et al. ............. 73/660 |
| 5,847,658 A | 12/1998 | Irie et al. ..................... 340/683 |
| 5,995,910 A | 11/1999 | Discenzo ..................... 702/56 |
| 6,092,029 A * | 7/2000 | Bently .......................... 702/56 |

FOREIGN PATENT DOCUMENTS

EP    0 908 805 A1    4/1999

(Continued)

OTHER PUBLICATIONS

X, Li et al. "Fault prognosis for large rotating machinery using neural" *Application of artificial intelligence in engineering IX. Proceedings of the ninth international conference, proceedings of ninth international conference on applications of artificial intelligence in engineering.* Aieng 94, Malvern, PA, USA 19-21 J, pp. 99-105.

(Continued)

*Primary Examiner*—Micheal Ngheim
*Assistant Examiner*—John Lee
(74) *Attorney, Agent, or Firm*—Oliff & Berridge PLC

(57) ABSTRACT

Novel tracked orders (i.e., tracked orders that are not present in "healthy" machinery) are useful for locating bearing anomalies. Accordingly, a method for locating bearing anomalies in machinery is provided that includes receiving vibration measurements acquired from the machinery, analyzing the vibration measurements to identify novel tracked orders indicative of bearing anomalies, and ascertaining the location of a bearing anomaly by relating a novel tracked order thus-identified to one or more further tracked orders. Thus, the novel tracked order does not merely indicate the occurrence of a bearing anomaly, but, in combination with the one or more further tracked orders, allows the bearing anomaly to be traced to a particular position.

10 Claims, 9 Drawing Sheets

FOREIGN PATENT DOCUMENTS

| | | |
|---|---|---|
| EP | 1 014 054 A2 | 6/2000 |
| GB | 2 135 061 A | 8/1984 |
| GB | 2 256 491 A | 12/1992 |
| GB | 2 277 151 A | 10/1994 |
| GB | 2 349 952 A | 11/2000 |
| WO | WO 02/03041 | 1/2002 |

OTHER PUBLICATIONS

X. Li et al. "Fault prognosis for large rotating machinery using neural network" *Application of artificial intelligence in engineering IX*. 19-21 J, pp. 99-105, Aieng 94.

Gelb et al., "Applied Optimal Estimation", *MIT Press* 1974, pp. 102-155.

Nairac et al., "A System for the Analysis of Jet Engine Vibration Data", *Integrated Computer-Aided Engineering*, vol. 6, No. 1, pp. 53-65, 1999.

Ghahramani et al., "Parameter Estimation for Linear Dynamical Systems", *Technical Report CRG-TR-96-2*, University of Toronto, Feb. 22, 1996, pp. 1-6.

Roweis et al., "A Unifying Review of Linear Gaussian Models", *Neural Computation*, vol. 11, 1999, pp. 305-345.

Ghahramani et al., "Learning Nonlinear Dynamical Systems using an EM Algorithm", in Kearns et al. (ed), *Advances in Neural Information Processing Systems*, vol. 11, MIT Press, 1999.

\* cited by examiner

Prediction Error for 70003098
(two weeks before bird strike)

BEARING ANOMALY DETECTION AND LOCATION

This application claims priority for U.S. Provisional Application No. 60/439,026 filed on Jan. 10, 2003, the disclosure of which is incorporated by reference.

FIELD OF THE INVENTION

This invention relates to methods and data processing systems for detecting and locating bearing anomalies. The methods and data processing systems of the invention are particularly, although not necessarily exclusively, suitable for detecting bearing anomalies in rotating machinery such as for example gas turbines, spark ignition and compression ignition internal combustion engines, and other types of power plant.

BACKGROUND

In order to determine the condition of machinery, it is normal to monitor and analyse a series of measurable "condition indicators" which themselves reflect aspects of the condition of the machine. This allows machine deterioration and/or problems to be detected and, if necessary, addressed at an early stage.

However, particularly with complex machinery such as gas turbine engines, the number of indicators that must be monitored to obtain an overall picture of the engine's condition can be high. This in turn means that the task of analysing the complete series of indicators to determine the condition of the engine can be a complex one.

Taking again the example of a gas turbine, it is known to collect performance and vibration data from the engine over time to be analysed off-line by one or more experts. Typically the performance data will be compared with simulated data for the same engine and, based on this comparison, an expert will form a view as to the health of the engine. Additionally, a small amount of vibration data will be reviewed, giving a superficial view of gross changes in engine behaviour. If a problem is detected, the vibration data may then be analysed in more detail, often by another expert, to look for any abnormal indications which might be symptomatic of underlying mechanical problems which could lead to a loss of performance and operability.

In WO 02/03041 (which is hereby incorporated by reference) we describe a system for monitoring complex machinery which incorporates a learnt model of normal behaviour and which can register abnormal events in real time.

Bearings are often critical parts of machinery and hence bearing performance can contribute to machinery condition. Defects in bearing surfaces can affect machine functioning and catastrophic bearing failure can even compromise safety. For example, the proper performance of the bearings which support and locate the rotating shafts of a multi-shaft gas turbine engine is integral to engine operation.

Machines with rotating components such as gas turbine engines are subject to vibratory forces at frequencies which are related to the angular velocity of the respective component. These frequencies are conventionally known as engine order forcing frequencies, each engine order corresponding to a rotational frequency of a particular component (or harmonic thereof) and exerting a corresponding vibratory force on the machinery.

The forces may arise because e.g. the machinery is out of balance on a particular shaft, stiffness irregularities in the machine components, and, in the case of a gas turbine engine, aerodynamic interactions between the engine blades. At a given speed of rotation, a number of these engine orders are generally activ and result in corresponding measurable vibration responses. A "tracked order" is a specific vibration response which is associated with a respective machine component. Tracked orders can be illustrated by plotting the frequency of the particular response against engine speed or time.

Conventional methods of bearing anomaly detection involve monitoring the energy of a vibration frequency that is known to be indicative of bearing defect, i.e. monitoring for the appearance of a specific tracked order. If energy exists at the frequency the bearing is faulted.

SUMMARY OF THE INVENTION

The present invention is at least partly based on the realisation that novel tracked orders (i.e. tracked orders that are not present in "healthy" machinery) are useful for locating bearing anomalies.

Accordingly, in one aspect the present invention provides a method for locating bearing anomalies in machinery, which comprises;
   receiving vibration measurements acquired from the machinery,
   analysing the vibration measurements to identify novel tracked orders indicative of bearing anomalies, and
   ascertaining the location of a bearing anomaly by relating a novel tracked order thus-identified to one or more further tracked orders.

Thus the novel tracked order does not merely indicate the occurrence of a bearing anomaly, but, in combination with the one or more further tracked orders, allows the bearing anomaly to be traced to a particular position.

In one embodiment, the further tracked orders comprise at least one side-band to the novel tracked order. This can allow the component of the machinery which has the anomalous bearing to be identified. For example, in the case of a multi-shaft gas turbine engine, the spacing between side-bands of a novel tracked order can be indicative of the engine shaft which is supported by the anomalous bearing.

In another embodiment, the further tracked orders comprise a tracked order associated with a component supported by the anomalous bearing. This can allow the part of the bearing which is anomalous to be identified. Again taking the example of a multi-shaft gas turbine engine, the ratio between the novel tracked order and a tracked order produced by an engine shaft which rotates within the anomalous bearing can be indicative of the part of the bearing (e.g. inner race, outer race or rolling element) which is defective or faulty.

Thus, if side-bands are initially used to identify a machine component supported by an anomalous bearing, the tracked order associated with that component can then be used to trace the anomaly to a part of the bearing.

The further tracked order may be obtained from analysis of the vibration measurements acquired from the machinery. However, this additional analysis step may not be necessary if the further tracked order is already characterised. For example, in the case of a multi-shaft gas turbine engine, the vibration response of each shaft as a function of engine speed is generally known.

The present inventors have also found that bearing abnormalities are susceptibl to being detected using a condition signature which incorporates vibration measurements.

Thus, it is a further general aim of the present invention to provide methods and data processing systems that facilitate analysis of condition indicators, including vibration measurements, in a manner such that bearing anomalies can be more readily detected.

Accordingly, a further aspect of the invention provides a method for detecting bearing anomalies in machinery, which comprises performing at each of a plurality of times the steps of:

constructing a condition signature from a plurality of condition indicators including (a) a plurality of vibration measurements acquired from the machinery or (b) one or more vibration measurements and one or more performance parameter measurements acquired from the machinery;

predicting a normal signature corresponding to the condition signature for the machinery without bearing anomalies;

comparing the condition signature with the normal signature; and registering a bearing anomaly if the condition signature differs from the normal signature by more than a predetermined threshold.

The term "signature", as used herein, pertains to the values of a plurality of condition indicators merged or fused into a unit or quantity such as a set, vector or scalar. In the example of a vector signature, the indicators may correspond to respective elements of the vector. In the example of a scalar signature, the magnitude of the scalar may be determined by a mathematical function which acts upon the indicator values.

By merging or fusing the condition indicators into a single signature in this manner, and providing a normal signature with which the fused data can be compared, the task of detecting bearing anomalies is greatly simplified. In particular, the detection process can be largely automated, removing, or at least minimising, the requirement for expert input. This in turn means that it becomes feasible to continuously monitor for bearing anomalies, and to provide useful information in real time.

When a bearing anomaly is detected, the method of the first aspect may be used to locate the anomaly.

Preferably, at least one of the vibration measurements is acquired in a frequency range in which novel tracked orders indicative of bearing anomalies are expected to occur.

The condition indicators that are combined to form the condition signature include at least one vibration measurement acquired from the machinery. However, the condition indicators may also include operational parameters such as speeds, pressures (e.g. gas pressures, oil pressures) and temperatures for example. Other useful parameters may include what might be conventionally thought of as control or status parameters. For convenience, such parameters will be referred to using the single label of "performance parameters" in the following text.

Preferably at least three condition indicators are used to construct the condition signature. More preferably at least 10 and even more preferably at least 20 condition indicators are used to construct the condition signature.

The normal signature for the machinery without bearing anomalies can be derived from a predefined model of the machinery that is being monitored. This model can itself be developed off-line and then fixed for the duration of the operation of the bearing anomaly detection method. More preferably, however, the model is designed to be refined as the method proceeds in order that it might be better tuned to the specific machinery.

Whichever approach is adopted, it is particularly preferred that the model is a "learnt model" developed using a data-driven, or at least partially data-driven approach. That is to say the learnt model learns from training data comprising series of the condition indicators which have been labelled as normal (i.e. without bearing anomalies) or abnormal (i.e. with bearing anomalies) as the case may be. In fact, it is often the case that normal data is far more readily available than abnormal data and therefore the training data may only include examples of normal data. This still results in an effective model, because bearing anomalies can then be identified as departures from the learnt model of normality.

The normal signature may be predicted from a model defining one or more inter-dependencies between the condition indicators. This enables the model to specify a continuous boundary in N-dimensional space (where each dimension relates to one of N condition indicators) corresponding to the limits of normal machine operation. This is in contrast to "look up table" approaches for setting the limits of normal machine operation which do not capture the (often complex) inter-relationships and correlations between condition indicators.

So, for example, it is often the case that the onset of a bearing problem or failure manifests itself in small changes to a number of condition indicators which individually, however, remain in their respective allowable ranges. The "look up table" approach, which is only able to sense gross shifts in individual parameters, would fail to recognise that a problem or failure had occurred. In contrast, when the condition signature is predicted from a model defining one or more inter-dependencies between the condition indicators the several small changes in the condition indicators may have the cumulative effect of driving the condition signature outside the normal boundary in N-dimensional space.

Preferably, the predetermined threshold corresponds to a statistically significant departure or variance from normality as defined by the normal signature. Thus, in the example of a normal signature provided by a learnt model, further development of the model (e.g. due to the input of more training data) will result in a corresponding variation in the predetermined threshold.

The model may comprise a matrix (e.g. a covariance matrix) with one or more non-zero off-diagonal terms to define the inter-dependencies. The step of comparing the condition signature with the normal signature may then involve calculating a value for the normalised innovations squared (NIS) which is defined below in the "Description of the Embodiments".

Alternatively, the model may comprise a neural network. If there are N condition indicators, one embodiment is a neural network which is trained to predict the value of the $N^{th}$ from the other N−1 indicators. The step of comparing the condition signature with the normal signature may then involve calculating a prediction error which is e.g. the square of the difference between the predicted value for N and the actual value. There may be N of these predictive networks operating in parallel for each of the condition indicators. In this case the total prediction error can be the sum of the prediction errors of each of the networks. In another embodiment, a neural network is trained to predict a subset of N1 condition indicators (such as vibration values, e.g. at a number of key frequencies) from another subset of N2 condition indicators (such as the performance parameters), where N1+N2=N.

Preferably the times define successive intervals of at most 1 sec duration (i.e. a 1 Hz repetition frequency). More preferably the times define successive intervals of at most 0.2 sec duration (a 5 Hz repetition frequency), even more preferably at most 0.1 sec (a 10 Hz repetition frequency). By acquiring and processing the condition indicator data at such rates, it is possible for the method to detect bearing anomalies in real time. Therefore, if an anomaly is registered at any time, immediate and appropriate action can be taken by the system operator. This can be particularly advantageous for the operation of safety critical plant such as aero gas turbine engines.

The data acquisition rate can, however, be significantly faster than the processing rate. For example the data acquisition rate may be in the range 20 Hz to 80 kHz. Only a subset of the acquired data may then be processed.

Where the condition signature is comprised of data from disparate sources, for instance performance and vibration data, a problem occurs if the data are not well synchronised in time as a distorted condition signature may result. For similar reasons, training data used to develop a model of normal machinery behaviour should also be synchronised if distortions in the model are to be avoided.

Thus preferably, the condition indicators are synchronously acquired from the machinery to a synchronisation imprecision of at most 1 sec. More preferably the synchronisation imprecision is at most 0.1, 0.075, 0.0625 or 0.02 sec. By "synchronisation imprecision" we mean the maximum difference between the acquisition times of each pair of condition indicators forming a particular condition signature. Desirably, the measurements are acquired from the machinery at a synchronisation imprecision which is less than the duration of the successive time intervals, e.g. if the time intervals are of 0.2 sec duration, the synchronisation imprecision may be at most 0.075 sec.

In a preferred embodiment of either of the previous aspects, the machinery is a gas turbine engine.

Further aspects of the invention provide (a) a computer system operatively configured to perform the method of either of the previous aspects, (b) computer readable media carrying computer code for performing the method of either of the previous aspects, and (c) a computer program for performing the method of either of the previous aspects.

By a "computer system" we mean the hardware, software and data storage devices used to detect or locate bearing anomalies. For example, a computer-based system of the present invention may comprise a central processing unit (CPU), input means, output means and data storage. Desirably the computer system has a monitor to provide a visual output display. The data storage may comprise RAM or other computer readable media.

By "computer readable media" we mean any medium or media which can be read and accessed directly by a computer e.g. so that the media is suitable for use in the above-mentioned computer system or for carrying computer code for performing the method of either of the previous aspects. The media include, but are not limited to: magnetic storage media such as floppy discs, hard disc storage medium and magnetic tape; optical storage media such as optical discs or CD-ROM; electrical storage media such as RAM and ROM; and hybrids of these categories such as magnetic/optical storage media.

One aspect of the invention provides a data processing system for locating bearing anomalies in machinery, comprising:
 a data receiver for receiving vibration measurements acquired from the machinery, and
 a processor for (a) analysing the vibration measurements to identify novel tracked orders indicative of bearing anomalies, and (b) ascertaining the location of a bearing anomaly by relating a novel tracked order thus-identified to one or more further tracked orders.

Another aspect of the invention provides a data processing system for detecting bearing anomalies in machinery, comprising:
 data acquisition devices for acquiring a plurality of condition indicators from the machinery at each of a plurality of times, the condition indicators including (a) a plurality of vibration measurements or (b) one or more vibration measurements and one or more performance parameter measurements;
 a processor for constructing a condition signature from said vibration measurements and for predicting a normal signature corresponding to the condition signature for the machinery without bearing anomalies;
 a comparator for comparing the condition signature with the normal signature; and
 a register for registering a bearing anomaly if the comparator indicates that the condition signature differs from the normal signature by more than a predetermined threshold.

The data processing system may further comprise a display for displaying (a) one or more of the condition indicators, (b) the result of the comparison of the condition signature with the normal signature and/or (c) an alert signal when the comparator indicates that the predetermined threshold has been transgressed (i.e. a bearing anomaly has been registered).

BRIEF DESCRIPTION OF THE DRAWINGS

The various aspects of the invention will be further described by way of example with reference to the accompanying drawings, in which:.

DESCRIPTION OF THE EMBODIMENTS

The first embodiment described below is an example of a methodology for locating bearing anomalies (such as inner/outer bearing track defects, cage defects, rolling element defects and squeeze-film bearing anomalies) in a gas turbine engine.

Figure 1:
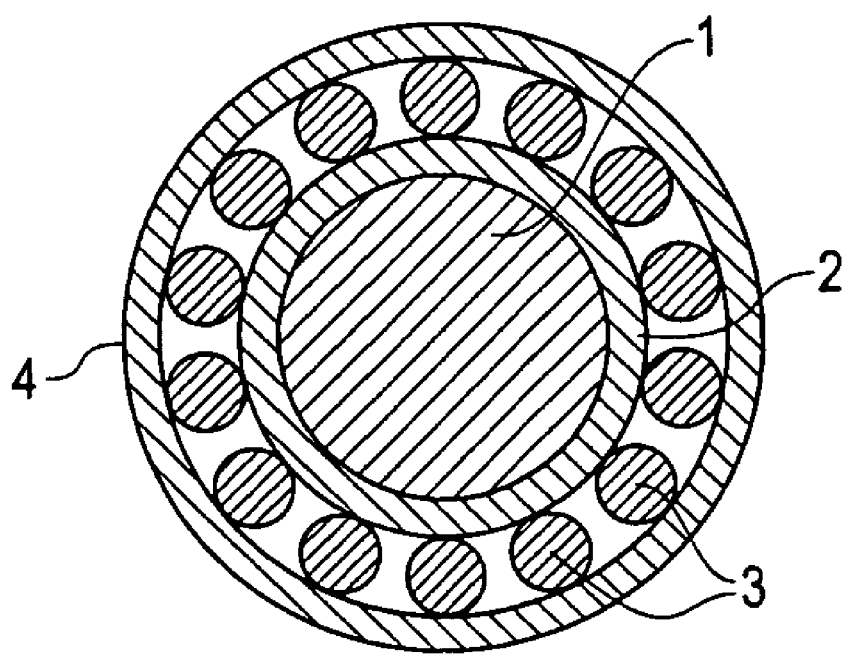
FIG. 1 shows a schematic transverse cross section of the high pressure (HP) shaft of a gas turbine engine.

FIG. 1 shows a schematic transverse cross section of the high pressure (HP) shaft 1 of the gas turbine. The shaft is located by a circular bearing which comprises an inner race 2, caged rolling elements 3 (cage not shown) and outer race 4. A defect can exist in either of the races or the cage and rolling elements.

Figure 2:
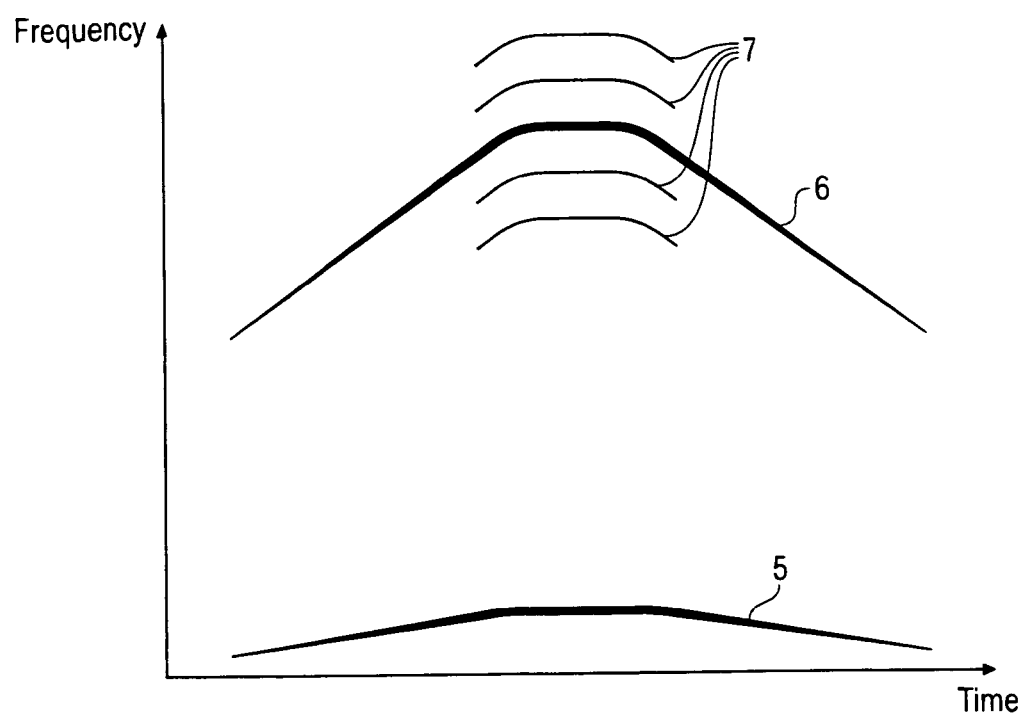
FIG. 2 shows a schematic plot of frequency against time for a fundamental tracked order and a higher frequency novel tracked order.

FIG. 2 shows a schematic plot of frequency against time for the fundamental HP tracked order 5 (which is also the HP shaft rotation frequency) and a higher frequency nov 1 tracked order 6. Both tracked orders are measured by vibration sensors attached to the engine. The upward and downward slopes of the tracked orders respectively correspond to an increase and decrease in engine speed, and the darkness of each tracked order line corresponds to the instantaneous vibration amplitude or energy.

The novel tracked order is in a frequency range that is characteristic of bearing anomalies, which of itself suggests the occurrence of a bearing defect. However, the present invention allows a more detailed diagnosis of the anomaly.

Firstly, we have found that the engine component with which the anomalous bearing is associated can be inferred by the side bands 7 to either side of the novel tracked order. In the present example each side band is spaced from the novel tracked order by a multiple of the fundamental HP tracked order, i.e. the side bands are the HP fundamental frequency and harmonics thereof added to or subtracted from the novel tracked order. From this it can be inferred that the anomalous bearing is associated with the HP shaft. If it had been associated with the intermediate pressure (IP) or low pressure (LP) shaft, the side bands would have been at spacings corresponding to the fundamental frequencies of these components.

Furthermore, we have found that where a novel tracked order is caused by a bearing anomaly, the ratio of the frequency of the novel tracked order to the fundamental frequency of the component supported by the bearing tends to remain constant. This provides further evidence for the location of the anomaly.

Figure 3:
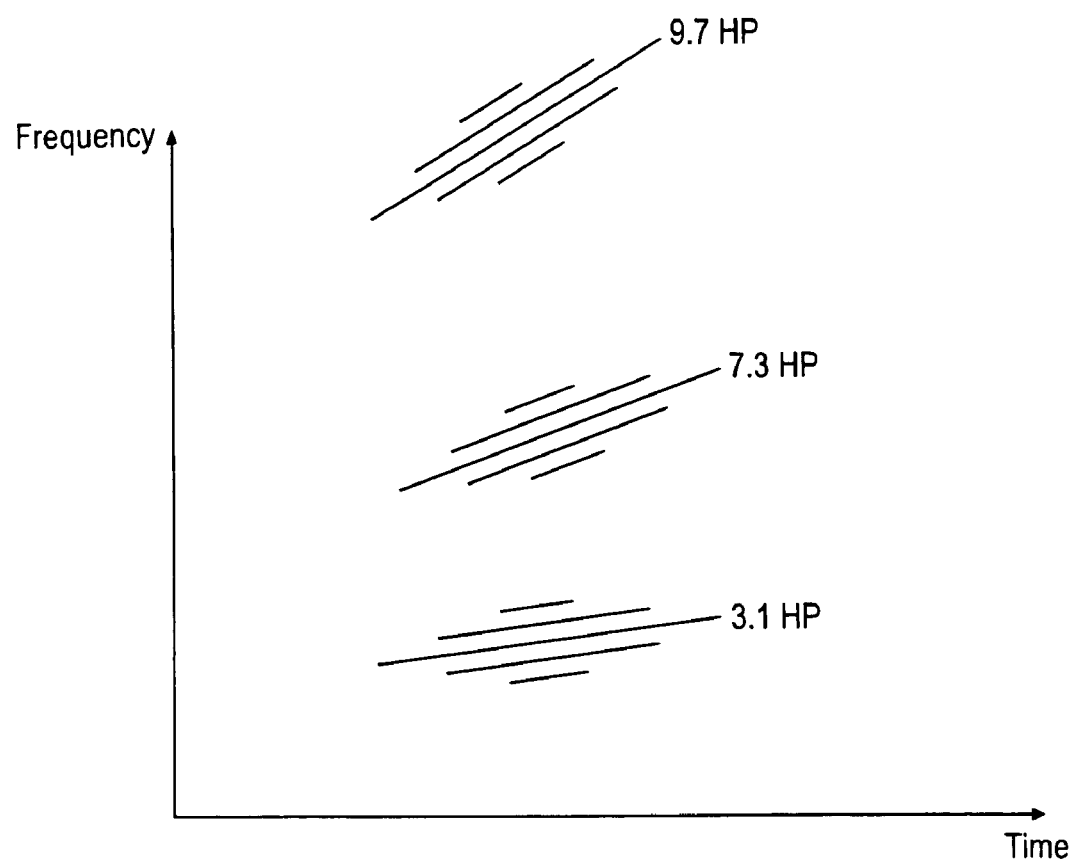
FIG. 3 shows a schematic plot of frequency against time for three novel tracked orders and respective side bands.

FIG. 3 shows a schematic plot of frequency against time for three novel tracked orders (and respective side bands) caused by bearing anomalies in bearings supporting an HP shaft. The tracked orders are labelled 9.7 HP, 7.3 HP and 3.1 HP, indicating the ratio of the respective novel tracked order to the fundamental HP tracked order. The value of the ratio is characteristic of where, in each bearing, the anomaly resides. In FIG. 3, 3.1 HP is a tracked order caused by a cage/rolling element defect, 7.3 HP is a tracked order caused by an inner race defect, and 9.7 HP is a tracked order caused by an outer race defect. The values are primarily dependent on the particular bearing component which is defective but not on the cause (e.g. wear, corrosion, foreign object incursion) or size of the defect.

We have observed constant ratio behaviour (albeit with different values for the ratios) between novel tracked orders and fundamental tracked orders for a wide range of bearing/shaft geometries.

Thus by relating novel tracked orders to side bands and fundamental frequencies it is possible to detect and locate bearing anomalies in complex machinery such as gas turbine engines.

The next embodiment described below is an example of a data processing system for synchronous acquisition, analysis and display of performance parameters and vibration data from a power plant (e.g. a gas turbine). The system may be used for detecting bearing anomalies in the plant. The anomalies may then be further analysed using the embodiment described previously.

The performance and vibration data streams are synchronised in real time and are combined or fused to construct a signature for the plant that can be compared to a signature derived from a model representing a healthy power plant, in order to provide anomaly detection.

The following discussion focusses on an application of the system to bearing anomaly detection in a gas turbine aero-engine, but it will be appreciated that the system can be adapted to other power plant, including for example ground-based and marine gas turbines, and spark ignition and compression ignition internal combustion engines, as well as other mechanical systems which make use of bearings.

The system acquires performance parameters from the gas turbine digitally via an ethernet link at a rate between 20 and 40 Hz. Typical performance parameters are measurements of pressure, temperature, thrust, altitude or Mach number. Vibration data are acquired from analogue vibration transducers which are sampled at user-selectable sampling rates (from 625 Hz to 80 kHz) via an analogue-to-digital converter. The amplitude spectrum of the vibration data in generated using the Fast Fourier Transform every 0.2 sec.

The performance and vibration data streams are asynchronous and stored in separate files together with the corresponding timestamps. During review, as data is loaded into memory, synchronisation is performed between the performance and spectrum data on a line by line basis. Markers 10,12 (see FIG. 4) are kept which record the last synchronized line in the vibration and performance data ring buffers 14,16. When new data is available in memory, the timestamp for the next vibration spectrum line is examined. The synchronisation algorithm starts from the last previously synchronised location in the performance data and searches forwards or backwards based on the timestamps of the performance data (accurate to 0.05 sec) until the closest matching timestamp in the performance data ring buffer 16 is identified. This location in the performance data is recorded as being synchronised with the line in the vibration ring buffer 14. The algorithm then proceeds to the next line in the vibration ring buffer 14 (0.2 sec later) and so on until there is no more data available to synchronise.

Clearly, therefore, if the performance parameters are acquired at 20 Hz (i.e. at 0.05 sec intervals) the synchronisation precision is 0.075 sec (i.e. half the acquisition interval added to the accuracy of the timestamps) and if the performance parameters are acquired at 40 Hz (i.e. at 0.025 sec intervals) the synchronisation precision is 0.0625 sec.

Figure 4:
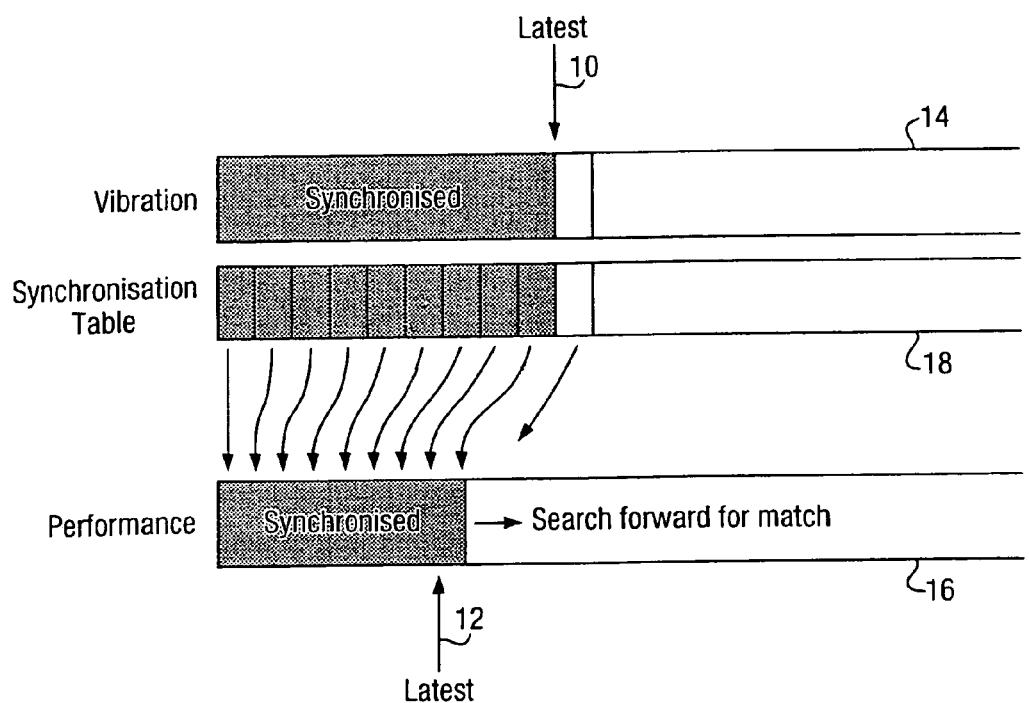
FIG. 4 schematically illustrates an exemplary data structure that can be adopted for operation of the invention.

Considering the synchronisation algorithm in a little more detail, it can be seen from FIG. 4 that the algorithm maintains a synchronisation table 18 that gives the index of the performance data entry that matches each vibration data line. The algorithm uses variables to mark the latest synchronised data in each buffer. The operation of the algorithm can be summarised by the following "pseudo code":

1. Initialise the latest synchronised markers to the start of the vibration and performance data.
2. Loop while there is more data in both ring buffers.
   (a) Starting from the latest synchronised data item in each ring buffer, examine the time stamp, t, on the next entry in the vibration ring buffer.
   (b) Search forward in the performance ring buffer until a time stamp greater than t is found. Select between this entry in the performance ring buffer and the previous entry for one which is closest to t and record the match in the synchronisation table.

Once synchronised, the analysis of the performance and vibration data relies on constructing models of normal jet engine behaviour and then detecting a bearing anomaly with respect to these models.

Traditional aircraft engine monitoring systems are based on two distinct processes; the use of vibration signatures to indicate engine state, and a separate procedure, gas-path analysis, which is employed for determination of state from performance parameters. In the approach described now, however, performance-related parameters such as pressure and temperature are fused with vibration data (such as tracked order vectors—the elements of which correspond to the signal amplitude in a narrow range centred on the main vibration frequencies for each shaft of the turbine). The aim is to take advantage of disparate sources of data to form a more comprehensive picture of engine state during normal operation. This in turn should allow a wider range of anomalies to be identified.

Furthermore, it is proposed to employ learnt data-driven models to model a normal engine. Thus, although models of the engine system are used, these are not fixed. Instead, they evolve with acquired training data. This offers the important advantage of robustness.

The methods of data analysis described below may be termed "novelty detection". An advantage of the methods is that the role of the expert need only be retained in classifying training data as abnormal (i.e. novel) or normal. The use of Kalman filtering systems in novelty detection has been described in e.g. M. Gelb, *Applied Optimal Estimation*. MIT Press 1974.

Two alternative data analysis methods are described below. They are distinguished by the amount of prior knowledge required to set up the system. In both cases, the role of the expert need only be retained in classifying training data as novel or normal.

The first method relies on a prior learnt model of normality. For example, normal vibration tracked order shapes are learnt using a simple clustering model for the normal data. The novelty of e.g. the vibration signature for an engine under test is assessed by comparing the closeness of its tracked order signature with the prototypical patterns in the clustering model of normality. This can be done, for example, by computing the shortest normalised Euclidean distance between the vector encoding the tracked order shaped to any of the (prototypical patterns) cluster centres in the model of normality (see Nairac et al, "A System for the Analysis of Jet Engine Vibration Data", *Integrated Computer Aided Engineering,* 6(1):53–65, 1999). If this distance is beyond a previously set threshold, the vibration signature as represented by that tracked order is deemed to be outside the bounds of normality. In addition to the vibration tracked orders, the model of normality for the vibration spectra includes the following: side-bands, multiple harmonics, fractional harmonics and broadband power.

Figure 5:
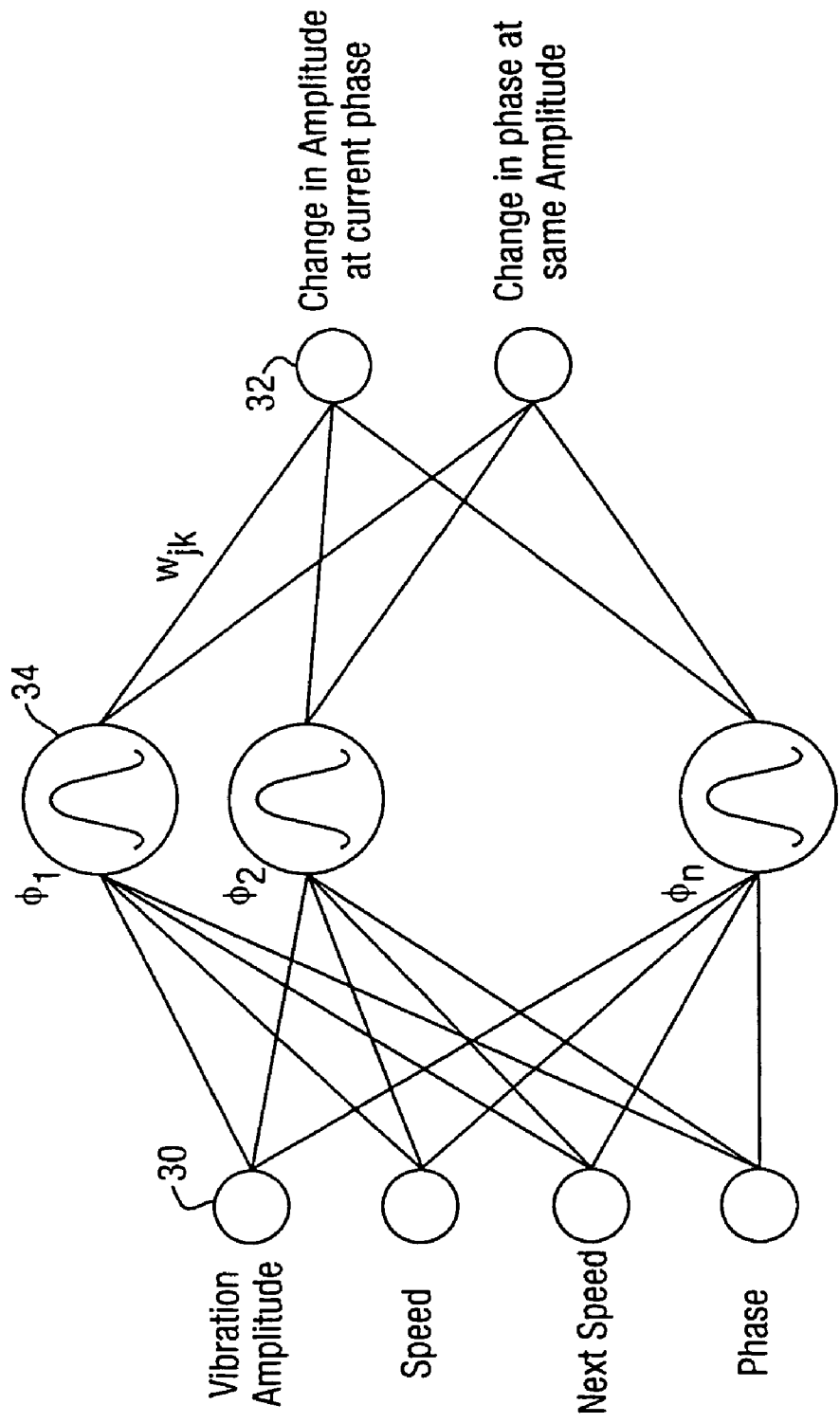
FIG. 5 shows a neural network architecture for a learnt model for operation of an aspect of the invention.

The model is illustrated by an example in which a neural network having the architecture shown in FIG. 5 was developed as the learnt model.

The neural network had an input layer 30 with four nodes for a condition signature consisting of four condition indicators measured relating to one shaft of a multi-shaft test engine. The condition indicators were the vibration amplitude, the phase and the shaft speed all at a specified time, and the shaft speed a time increment after the specified time.

The output layer 32 of the network had two nodes for predicting respectively the change in vibration amplitude and change in phase after the time increment.

The network had one hidden layer 34, each node of which contained a Gaussian radial basis function.

The training phase for network used training data obtained from the test engine over a range of normal operating conditions. The centres and the spreads of the Gaussians were fixed using the cluster analysis described above and the weights of the connections between the nodes were then iteratively adjusted until the model converged.

Figure 6:
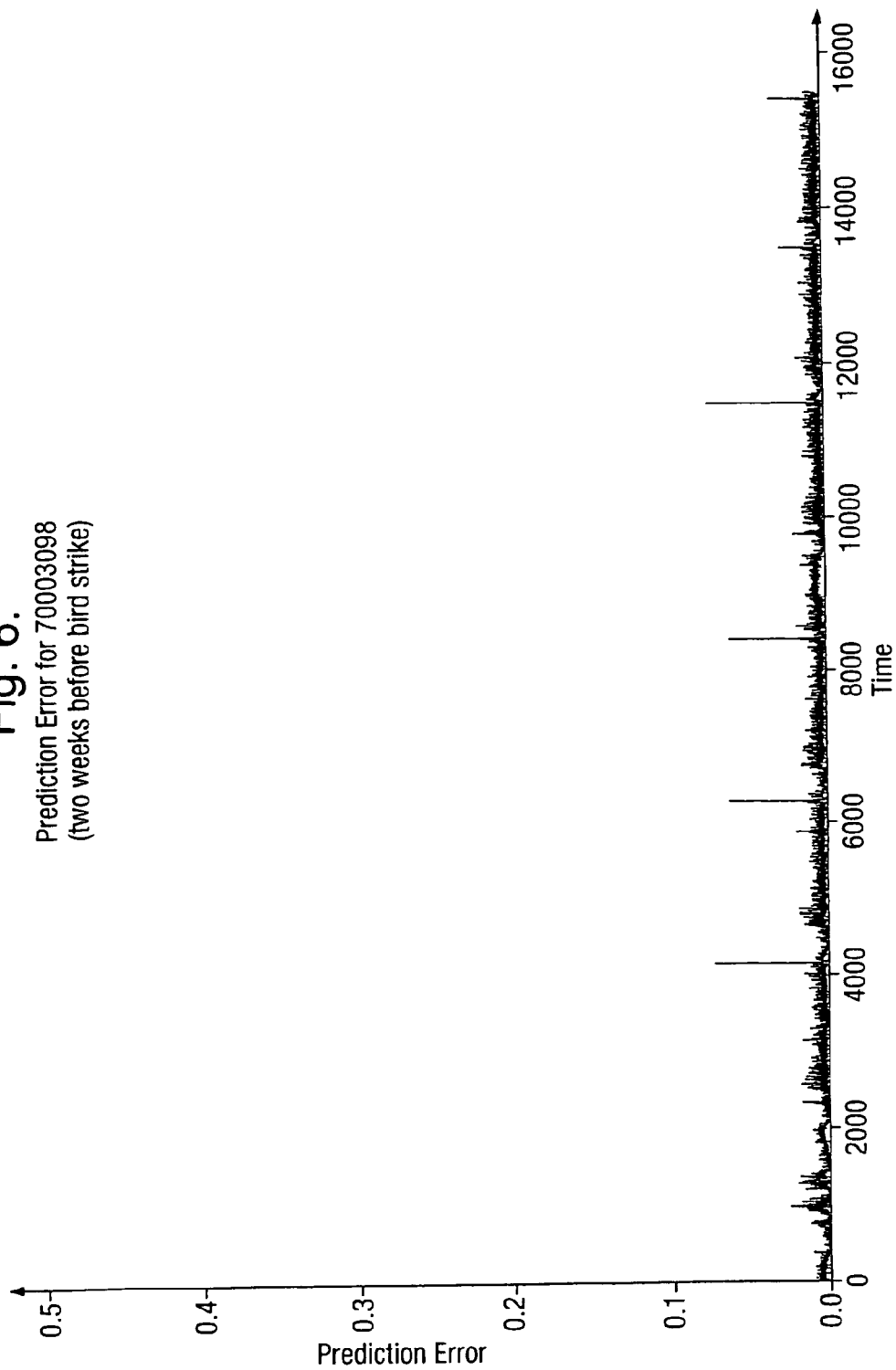
FIG. 6 shows a graph of the prediction error for the learnt model on a set of test data corresponding to a period of normal operating conditions for an engine.

FIG. 6 shows a graph of the prediction error (i.e. the sum of the prediction errors of the change in vibration amplitude and change in phase) for the model on a set of test data which also corresponded to a period of normal operating conditions for the engine. This graph provides a baseline of prediction error variation against which novel events can be judged.

Figure 7:
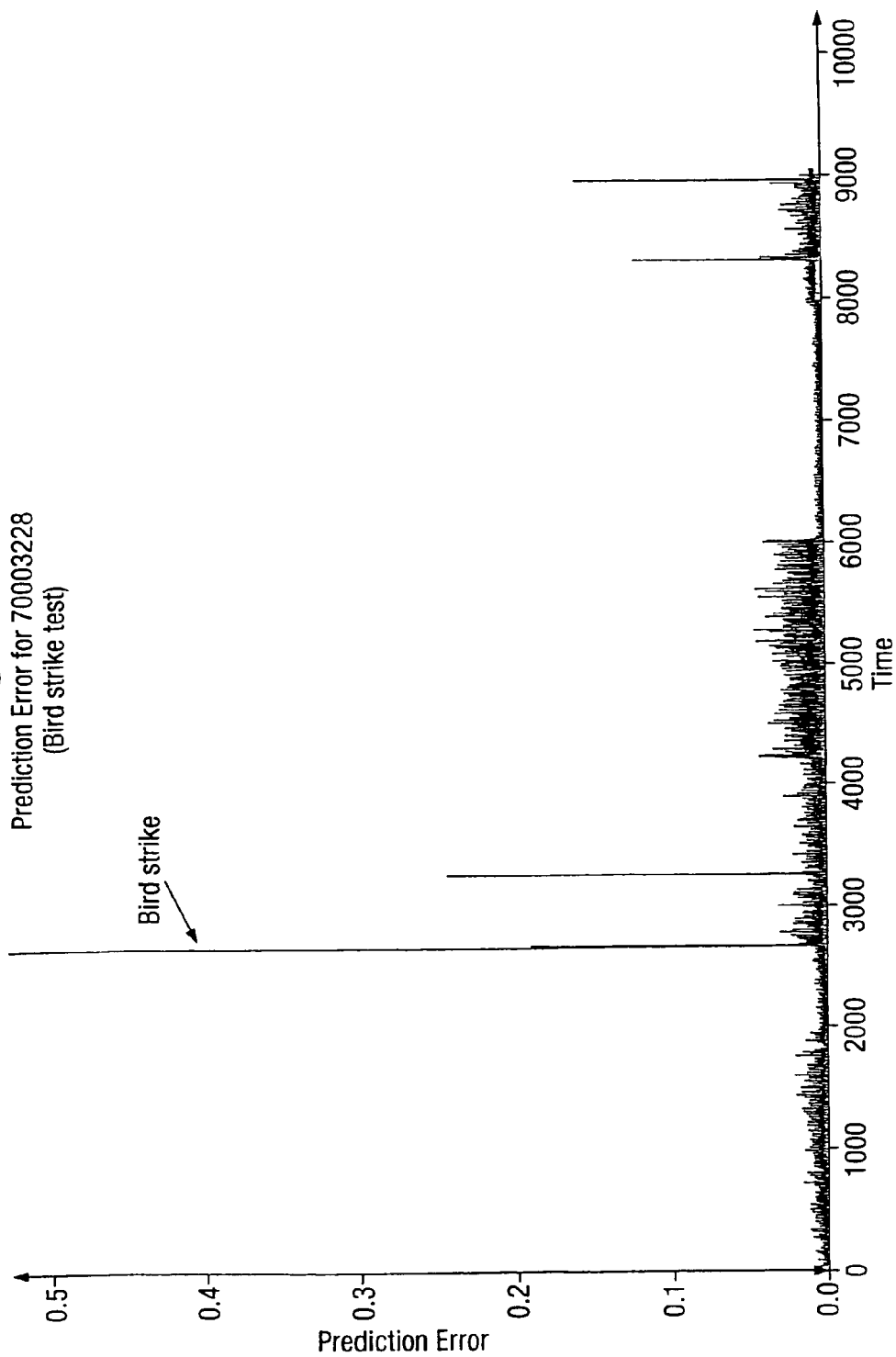
FIG. 7 shows a graph of the prediction error for the learnt model for a further engine operating period in which the engine experienced a bird strike.

FIG. 7 shows a graph of the prediction error for a further engine operating period. In this case, however, the engine experienced a bird strike. The largest peak in the graph corresponds to the moment of bird impact. Clearly the model was able to recognise this event. However, the changed prediction error signal (compared to the baseline of FIG. 6) after the event showed that the model was also able to detect post-impact abnormal engine behaviour. This provides confidence that the model can not only detect major events such as bird strikes, but also more subtle deviations from normality such as might be caused by bearing anomalies.

The second method employs a process model which has a state vector associated with it (see below). The observation vector (i.e. the condition signature) has elements corresponding to measured values of performance parameters and vibration information so that two types of data are fused within the model. The fusion of the data is performed in real-time with a new output being generated by the system several times a second.

An important aspect of the use of this model in the system is the use of learning. In a first, off-line, phase of learning, a generic model of the engine is learnt. The learning is data-driven using an algorithm such as Expectation-Maximisation in order to maximise the likelihood of the learnt model given the training data. Once such a generic model has been learnt off-line for a particular type of engine, learning can then be applied on-line in order to tune the model to an individual engine immediately after its pass-off test and after each maintenance procedure. Engine deterioration can also be learnt on-line. The learnt model can be tuned to different flight conditions, such as cruising or landing, in order to detect novelty with even more sensitivity and specificity.

The data-driven learnt model may be integrated with existing performance models which rely on the laws of thermodynamics and computational fluid dynamics (knowledge-based models). Such models can therefore be described as hybrid models because they are based on the integration of learnt and knowledge-based models.

Looking in more detail at the learnt modelling approach, it is based on the application of Expectation Maximisation (EM) to parameter estimation in linear dynamical systems (see Ghahramani and Hinton, *Parameter Estimation for Linear Dynamical Systems,* Technical Report CRG-TR-96-2, University of Toronto, 1996) and to non-linear systems (see Roweis and Ghahramani, "A Unifying Review of Linear Gaussian Models", *Neural Computation,* 11, 305-345, 1999; and Ghahramani and Roweis, "Learning in Nonlinear Dynamical Systems Using an EM Algorithm" in Kearns et al. (editors), *Advances in Neural Information Processing Systems,* Volume 11, MIT Press, 1999).

The EM learning algorithm is applied to a Kalman filter model. In the linear case, this is a system with a measurement process of the form $$y(i)=Cx(i)+v(i) \qquad (1)$$

where y(i) is a set of observations of hidden state x(i), C is a covariance matrix, and measurement noise v(i) is zero-mean and normally distributed with covariance matrix R. y(i) and x(i) can be the same dimension. Non-zero off-diagonal terms in C allow the model to account for interdependencies between the performance parameter and vibration measurements of the condition and normal signatures. The state equation is $$x(i+1)=Ax(i)+w(i) \quad (2)$$

with w(i) zero-mean and normally distributed with covariance matrix Q.

At the beginning of the training phase A and C are initialised to small random values (e.g. with elements of the matrices $10^{-5}$), and R and Q are initialised e.g. to I.

Then during the training phase, for each condition signature y(i) in the training set, the method of Roweis and Ghahramani applied to equation (2) to derive the most likely values for the elements of x(i), and the elements of C, R and v(i) are iteratively adjusted so that Cx(i)+v(i) converges to the respective condition signature (R and Q can be constrained throughout to be diagonal matrices). Convergence can be determined by the log-likelihood of the set of observations given the model.

Instead of initialising the elements of A to small random values, it is also possible to adopt initial values that embody existing performance models of engine behaviour. After the training phase, the model would then be a hybrid of a knowledge-based and a data-driven model. By fusing these two methods of data-analysis, the accuracy of prior expert knowledge can be combined with the robustness of data-driven approaches.

When the training phase has ended and the model is receiving real-time data consisting of a sequence of condition signatures, the Kalman filter is again used to derive the most likely values for the elements of x(i) for each condition signature y(i). However, the elements of C and v(i) are now fixed, so Cx(i)+v(i) provides the normal signature for comparison with the condition signature.

For example, comparison of the normal signature with the condition signature can be on the basis of the normalised innovations squared (NIS). The innovations sequence v is the difference between the condition signature and the normal signature, so $$v(k)=y(k)-C\hat{x}(k|k-1) \quad (3)$$

The innovations should be zero-mean and white.

The NIS combines the individual innovations sequences.

$$NIS(k)=v^T(k)S(k)^{-1}v(k) \quad (4)$$

The individual sequences are weighted by the term $S(k)^{-1}$, the inverse of the innovation covariance given by $$S(k)=C(k)P(k|k-1)C(k)^T+R(k) \quad (5)$$

where P(k|k−1) is the prediction covariance.

The model is first illustrated by a simple example (which does not use vibration measurements) where observations are made of the speeds of the three shafts of a test engine during cruise. The observed data y is simply the state x corrupted by noise, so $$y(i)=x(i)+v(i) \quad (6)$$

The observations are used during the learning process, to generate a dynamical system model in which A, C, Q and R are learned from the data. At the beginning of the training phase A and C were initialised to small random values and R and Q were initialised to I.

Figure 8:
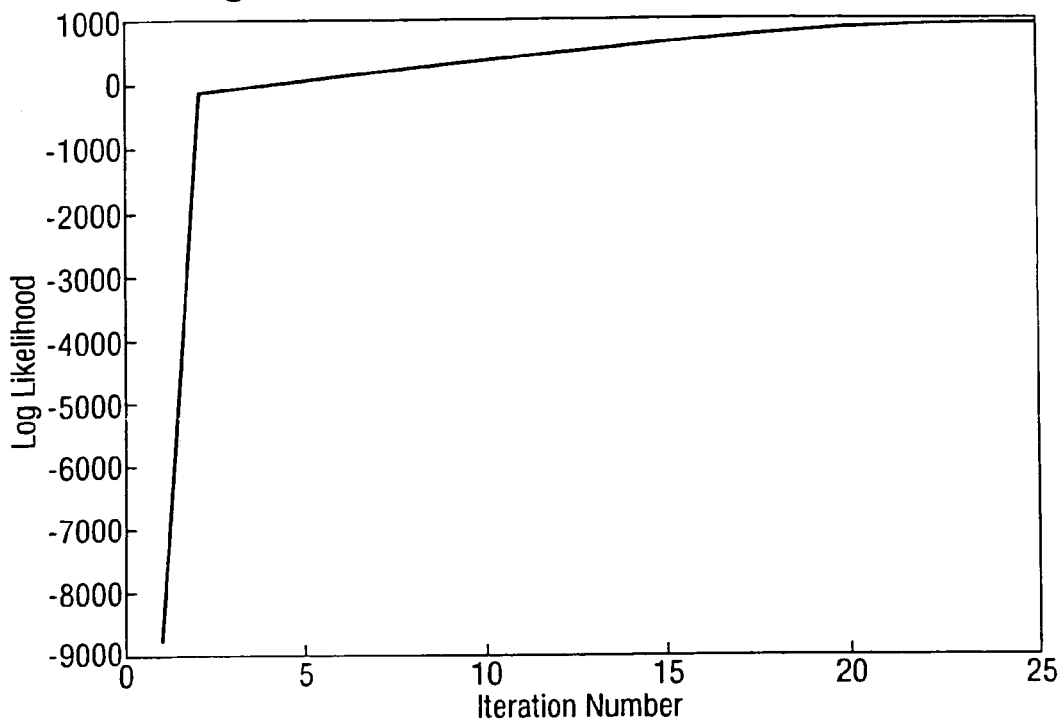
FIG. 8 shows the learning curve of a system model for operation of an aspect of the invention.
Figure 9:
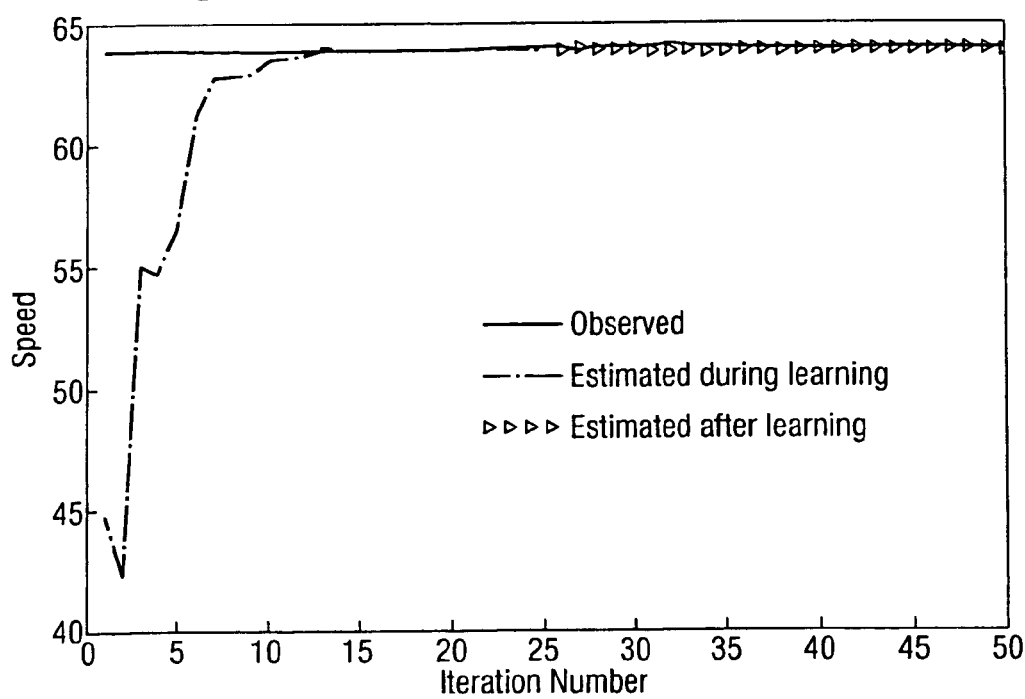
FIG. 9 shows a comparison of observations and modelled estimates for a shaft speed measurement, illustrating evolution of the model of FIG. 8.

FIG. 8 illustrates the learning (log likelihood) plot for the system. FIG. 9 shows the evolution of estimates of shaft 1 speeds during the learning process using the EM algorithm. In the example shown, the learning stage lasts for the first 25 iterations. From iteration 25 onwards, the system's dynamical properties are determined by the learned matrices (which are then kept fixed).

Once trained on vibration measurements, the system can be used to detect bearing anomalies which appear as divergences from the learnt model of normality. However, particularly where the models have been learned only for "steady state" parts of the flight envelope (e.g. acceleration, cruise and deceleration), transients during operation of the engine will also be flagged up as events, although they are expected. For example, where a bleed valve is opened or closed, the operating condition of the engine will exhibit significant differences from a learnt model of steady state normality which does not include this event.

Thus when using such a steady state model, measures can be employed to avoid these transient events. For instance, since the opening of a bleed valve is an event that occurs at a defined point in time, the data collected from the engine at that time and slightly either side of it (e.g. for 2 seconds before and after) can be eliminated from the data analysed by the health monitoring system.

Next we consider how a monitoring system, incorporating the models described above, could be installed for in-flight analysis of aero gas turbines and for performing in bearing anomaly location.

Figure 10:
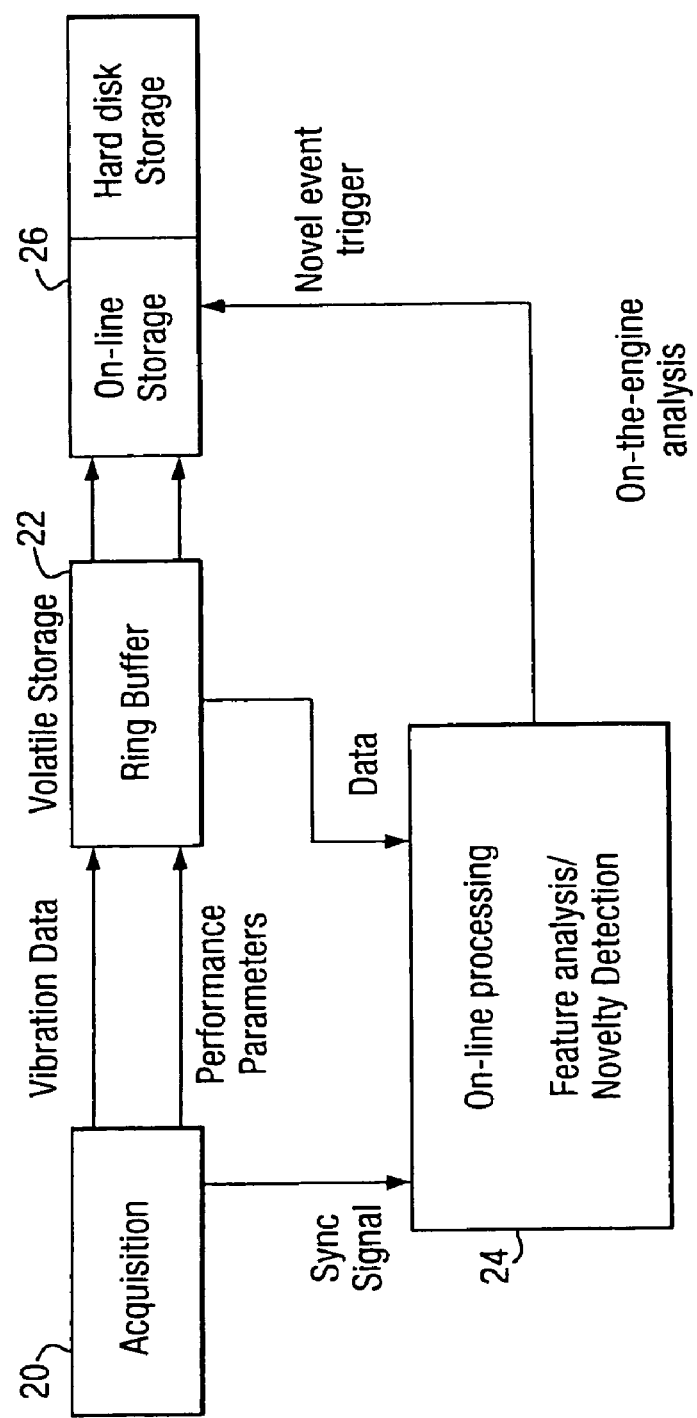
FIG. 10 shows a schematic example of an on-the-engine bearing anomaly detection system.

An on-the-engine system, shown schematically in FIG. 10, could generate of the order of 1 Gb of vibration and performance data (consisting mainly of pressures, temperatures and shaft speeds) per flight. The vibration data is usually analysed in the frequency domain. The vibration and performance data, as they are being generated by data acquisition means 20, are temporarily stored in ring buffer 22. The data is synchronised and subjected to novelty detection in processor and comparator 24 which receives a synchronisation signal from data acquisition means 20 and the data from ring buffer 22. Those sections of the data corresponding to novel events are then tagged and recorded with no loss of information (i.e. high bandwidth data is recorded) in registration means 26 which has semi-permanent on-line and/or hard disk storage. When the flight is completed the stored data may be downloaded and subjected to more intensive ground-based analysis.

For example, if the novel event is indicative of a bearing anomaly, the vibration data may include a novel tracked order. The same or a further processor can then identify the likely location of the bearing anomaly by determining (a) the fundamental frequency producing side bands to the novel tracked order and (b) the ratio of the novel tracked order frequency to the fundamental frequency.

The system may also include a display which is driven to allow information to be displayed either during acquisition or for review once an acquisition cycle has been completed. It preferably includes the following features:

Ability to display the result of the comparison of the condition signature with the normal signature, e.g. in the form of the NIS or the prediction error. An anomaly may be highlighted e.g. with an alert signal.

Ability to display a combination of any two of vibration spectra, tracked orders, broadband power, performance parameters synchronised in time.

Ability to extract and plot vibration spectra and tracked orders against engine speed.

Ability to interrogate and print any of vibration spectra, tracked orders, broadband power and performance parameters.

Automatic detection and display of features from vibration spectra and tracked orders (side bands, harmonics, etc.)

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

The invention claimed is:

1. A method for detecting bearing anomalies in machinery, which comprises performing at each of a plurality of times the steps of:

constructing a condition signature from a plurality of condition indicators including (a) a plurality of vibration measurements acquired from the machinery or (b) one or more vibration measurements and one or more performance parameter measurements acquired from the machinery;

predicting a normal signature corresponding to the condition signature for the machinery without bearing anomalies;

comparing the condition signature with the normal signature; and registering a bearing anomaly if the condition signature differs from the normal signature by more than a predetermined threshold.

2. A method according to claim 1, wherein the normal signature is predicted from a model defining one or more inter-dependencies between the condition indicators.

3. A method according to claim 2, wherein the model is a learnt model.

4. A method according to claim 2, wherein the model comprises a matrix with one or more non-zero off-diagonal terms to define said inter-dependencies.

5. A method according to claim 4, wherein the step of comparing the condition signature with the normal signature involves calculating a value for the normalized innovations squared.

6. A method according to claim 2, wherein the model comprises a neural network.

7. A method according to claim 6, wherein the step of comparing the condition signature with the normal signature involves calculating a prediction error.

8. A method according to claim 1, wherein said times define successive intervals of at most 1 sec duration.

9. A method according to claim 1, wherein the machinery comprises a gas turbine engine.

10. A data processing system for detecting bearing anomalies in machinery, comprising:

data acquisition devices for acquiring a plurality of condition indicators from the machinery at each of a plurality of times, the condition indicators including (a) a plurality of vibration measurements or (b) one or more vibration measurements and one or more performance parameter measurements;

a processor for constructing a condition signature from said vibration measurements and for predicting a normal signature corresponding to the condition signature for the machinery without bearing anomalies;

a comparator for comparing the condition signature with the normal signature; and a register for registering a bearing anomaly if the comparator indicates that the condition signature differs from the normal signature by more than a predetermined threshold.

* * * * *